United States Patent
Heine et al.

(10) Patent No.: US 9,427,188 B2
(45) Date of Patent: Aug. 30, 2016

(54) SPACER ATTACHMENT FOR A DERMATOSCOPE

(71) Applicant: Heine Optotechnik GmbH & Co KG, Herrsching (DE)

(72) Inventors: Oliver Heine, Herrsching (DE); Wolfgang Behrendt, Seefeld (DE); Roman Raab, Herrsching (DE)

(73) Assignee: Heine Optotechnik GmbH & Co KG, Herrsching (DE)

( * ) Notice: Subject to any disclaimer, the term of this patent is extended or adjusted under 35 U.S.C. 154(b) by 581 days.

(21) Appl. No.: 13/968,928

(22) Filed: Aug. 16, 2013

(65) Prior Publication Data

US 2014/0066727 A1 Mar. 6, 2014

(30) Foreign Application Priority Data

Sep. 4, 2012 (DE) .................... 20 2012 008 449 U

(51) Int. Cl.
*A61B 5/00* (2006.01)
*G02B 25/02* (2006.01)

(52) U.S. Cl.
CPC ............. *A61B 5/441* (2013.01); *A61B 5/0077* (2013.01); *A61B 2560/0443* (2013.01); *G02B 25/02* (2013.01)

(58) Field of Classification Search
CPC ...................................... A61B 5/441
See application file for complete search history.

(56) References Cited

U.S. PATENT DOCUMENTS

| | | | |
|---|---|---|---|
| 3,987,461 A * | 10/1976 | Kondo | ..................... G03B 7/18 352/141 |
| 6,032,071 A | 2/2000 | Binder | |
| 6,106,457 A | 8/2000 | Perkins et al. | |
| 6,118,476 A | 9/2000 | Morito et al. | |
| 6,907,138 B1 * | 6/2005 | Hoffman | ............ G01N 21/8806 382/154 |
| 7,167,243 B2 | 1/2007 | Mullani | |
| 7,220,254 B2 | 5/2007 | Altshuler et al. | |

(Continued)

FOREIGN PATENT DOCUMENTS

| | | |
|---|---|---|
| DE | 20022603 U1 | 2/2002 |
| DE | 10244875 B3 | 2/2004 |

(Continued)

OTHER PUBLICATIONS

European Search Report for European Patent Application No. 13179537 dated Dec. 23, 2013.

(Continued)

*Primary Examiner* — Christian Jang
(74) *Attorney, Agent, or Firm* — Bachman & LaPointe, P.C.

(57) ABSTRACT

The spacer attachment for a dermatoscope comprises an outer sleeve (12) including an attachment end configured for releasable attachment to the illumination head of a dermatoscope and a contact end intended to be placed on the skin of a patient at an examination location. A filter insert (30) is releasably attached in the outer sleeve (12) by rotation about the central axis of the outer sleeve (12), wherein the filter insert (30) includes a viewing plate (52) intersected perpendicularly by the central axis of the outer sleeve (12). The filter insert (30) is releasably attached to the outer sleeve (12) by a rotation snap device comprising at least one resilient snap hook (44) which is arranged at the outer circumference of the filter insert (30) and resiliently engages around a projection (26) provided at the inner wall of the outer sleeve (12).

14 Claims, 2 Drawing Sheets

(56) References Cited

U.S. PATENT DOCUMENTS 7,986,987 B2 7/2011 Bazin et al.
2013/0053701 A1 2/2013 Wiest et al.

FOREIGN PATENT DOCUMENTS

| DE | 102009044962 A1 | 4/2011 |
| JP | 5152799 A | 6/1993 |
| JP | 11155815 A | 6/1999 |
| JP | 2003126066 A | 5/2003 |
| WO | 9616698 A2 | 6/1996 |

OTHER PUBLICATIONS

Japanese Decision to Grant for 2013-183029.

* cited by examiner

SPACER ATTACHMENT FOR A DERMATOSCOPE

BACKGROUND OF THE INVENTION

The invention relates to a spacer attachment for a dermatoscope comprising an outer sleeve having an attachment end configured for releasable attachment to an illumination head of a dermatoscope, and a contact end intended to be placed on a skin of a patient at an examination location. The invention further relates to a kit and a dermatoscope comprising the spacer attachment.

Dermatoscopes include a magnifying optical system, a light source illuminating the region to be examined with as few reflections as possible as well as a power supply providing electrical energy to the light source. During a medical examination the dermatoscope is normally placed with a contact plate made of glass on the skin which is then observed through the optical system. In certain embodiments dermatoscopic oil or another liquid having a glass-like refractive index is placed between the skin and the dermatoscope, or the contact plate. Other embodiments make use of polarized illumination which means that neither a contact plate nor the application of dermatoscopic oil are required. Some medical diagnoses are only possible if the region to be examined is viewed using polarized illumination, while others can only be made without polarized illumination. Therefore it is advantageous if the dermatoscope can be operated using both types of illumination techniques. For this reason particular attention has been given to the development of a corresponding apparatus which is capable of employing both illumination techniques without great effort.

U.S. Pat. No. 7,167,243 B2 discloses a dermoscopy device capable of performing both illumination techniques. An annular polarizer filter having several recesses is positioned in front of a plurality of luminous diodes arranged in a circular ring. Some luminous diodes are placed—as seen in their illumination direction—in front of the recesses and some in front of the polarizer filter. An electronic circuit enables to engage a switch for initiating either polarized lighting or unpolarized lighting such that both illumination techniques are possible. The polarizer filter, which is arranged on the viewing axis, cannot be exchanged, which means that only certain medical diagnoses are feasible. A further disadvantage of the polarizer filter on the viewing axis is that it has a dampening effect of about 40% on the brightness in viewing. In addition, many polarizer filters are not color neutral such that even if a diagnosis without polarization is principally feasible, the polarizer filter produces an unnatural color tint which could impair the diagnosis.

DE 200 22 603 U1 discloses a dermatoscope having a generic spacer attachment. The dermatoscope includes a handle portion incorporating the power supply for a light source. The handle portion is provided with an illumination head having a viewing port extending therethrough in which a magnifiying lens is positioned. A plurality of luminous diodes is provided at the bottom end side of the illumination head at equal circumferential intervals about the viewing port. Furthermore a spacer attachment is attached to the bottom end side of the illumination head, including a contact glass at its bottom end which is placed on the skin of a patient during a medical diagnosis.

The object underlying the invention is to provide a spacer attachment for a dermatoscope using means of simple design which enables a user to optimally adapt the dermatoscope without great effort to many different kinds of diagnoses.

SUMMARY OF THE INVENTION

This object is achieved by a spacer attachment for a dermatoscope, comprising an outer sleeve having an attachment end configured for releasable attachment to an illumination head of a dermatoscope, and a contact end intended to be placed on a skin of a patient at an examination location, wherein a filter insert is releasably attached in said outer sleeve by rotation about a central axis of said outer sleeve and by means of a rotation snap device comprising at least one resilient snap hook which is arranged at the outer circumference of said filter insert and resiliently engages around a projection provided at an inner wall of said outer sleeve, said filter insert including a viewing plate intersected perpendicularly by said central axis of said outer sleeve.

The filter insert can be simply detached from the outer sleeve by rotation about the central axis and be replaced by a new filter insert which is advantageous for a new diagnosis.

For optimal lighting the filter insert includes a window ring surrounding the viewing plate and having several light-transmissive illumination windows arranged therein.

When the spacer attachment is attached to a corresponding dermatoscope, each of the light-transmissive illumination windows is arranged in front of an illuminant, preferably an LED.

An illumination polarizer filter can be arranged in the illumination windows, and a viewing polarizer filter can be arranged in the viewing plate. In a preferred embodiment, the illumination polarizer filters are cross-polarized relative to the viewing polarizer filter.

The contact end of the outer sleeve can be closed by a transparent contact plate, as it is the case in the dermatoscope known from DE 200 22 603 U1.

In order to perform different types of diagnoses, it is appropriate to provide a kit for a spacer attachment comprising several mutually exchangeable filter inserts. The filter inserts can, for example, be provided with a linear polarizer filter and/or a neutral density filter and/or a circular polarizer filter and/or a band-pass filter and/or a fluorescence filter.

A dermatoscope comprises a spacer attachment according to the invention at its illumination side. It is preferred to arrange each of a plurality of illuminants, preferably LEDs, at the illumination side of the illumination head—as seen in the illumination direction of each illuminant—in front of a respective window of the filter insert.

BRIEF DESCRIPTION OF THE DRAWINGS

Hereinafter an exemplary embodiment of the invention will be described in more detail with reference to the accompanying drawings, in which.

DETAILED DESCRIPTION

Figure 1:
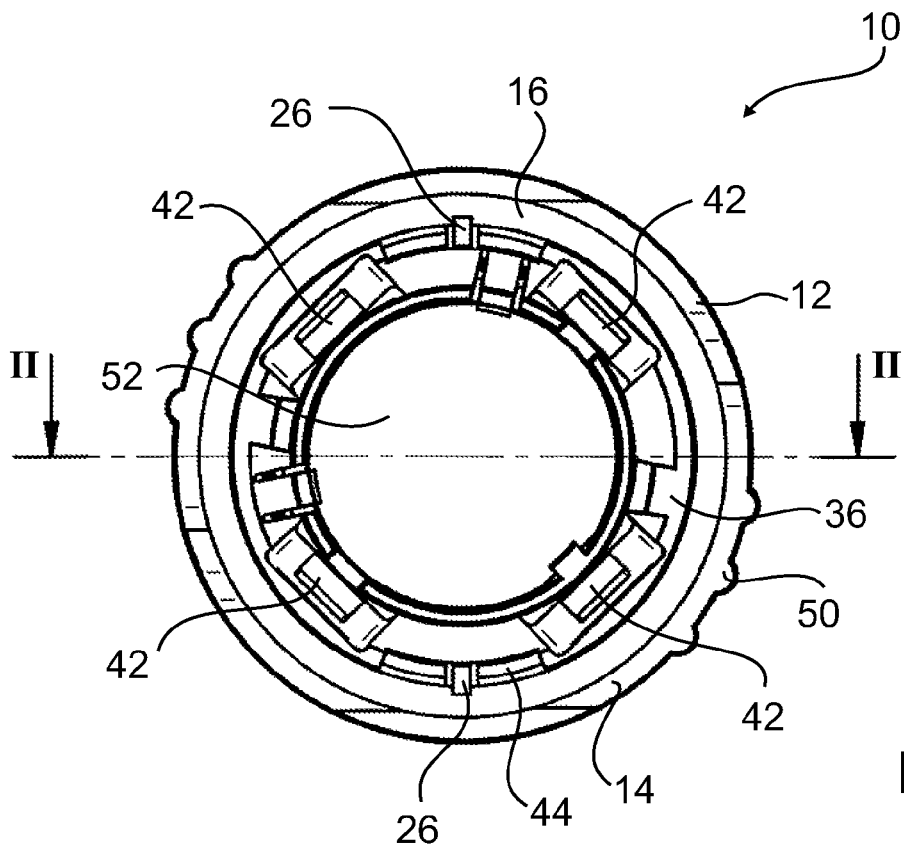
FIG. 1 is a bottom view of a spacer attachment.
Figure 2:
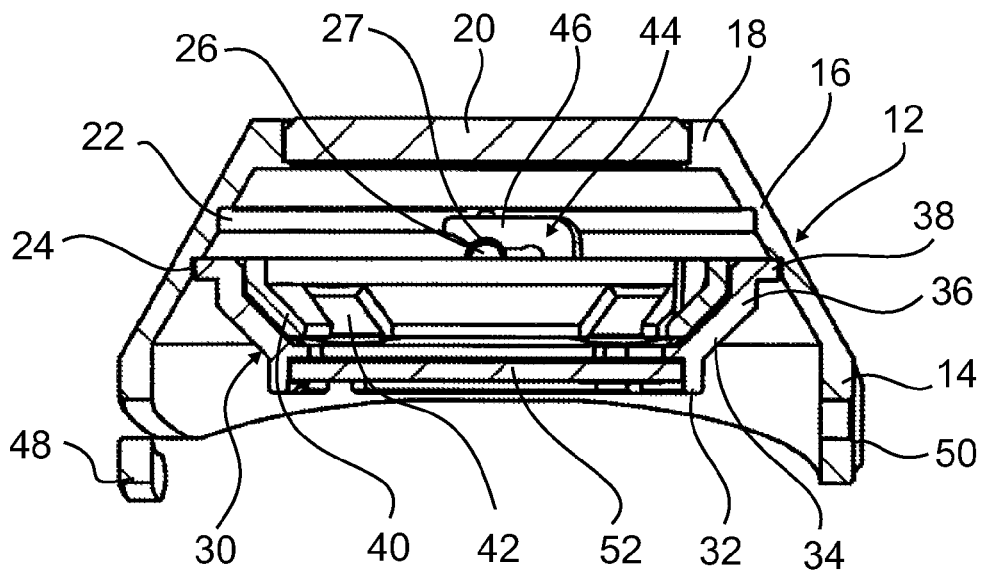
FIG. 2 is a cross-sectional view along line II-II of FIG. 1.

The spacer attachment 10 includes a substantially rotationally symmetric outer sleeve 12 comprising a substantially cylindrical lower portion 14 facing the illumination side of a dermatoscope 60 (FIG. 3), which is followed by a cone portion 16 having an upward conical taper. A light-transmissive contact plate 20 is inserted in the upper end side of the outer sleeve.

A lower cylindrical annular recess 24 is formed at the inner wall of the conical portion 16 of the outer sleeve 12, thereby defining a step. A further cylindrical annular recess 22 is located between the contact plate 20 and the annular recess 24.

Ribs 50 are provided at the outside of the cylindrical portion 14 of the outer sleeve 12 to facilitate rotation of the outer sleeve 12 for attaching it to the illumination head of a dermatoscope. Furthermore a circumferentially extending locking hook 48 is provided which snappingly engages in a corresponding recess at the illumination head during rotational attachment of the outer sleeve 12 to the illumination head.

A substantially rotationally symmetric filter insert 30 is inserted in the outer sleeve 12. The filter insert 30 includes an upper annular portion 38 which engages in the cylindrical annular recess 24. The annular portion 38 is followed in a downward direction by a coaxial cylindrical portion 36 of a smaller diameter, which passes into a cone portion 34 having a downward conical taper, which is in turn followed by a further coaxial cylindrical portion 32. A viewing plate 52 is held in the cylindrical portion 32. An annular window insert 40 is provided within the filter insert 30, abutting on the inside of the filter insert 30 in the region of the annular portion 38 and the cone portion 34. Windows 42 are formed in the window insert 40 in the region of the cone portion 34, each of which is arranged in front of an LED in an illumination head when the spacer attachment 10 is attached to the illumination head of a dermatoscope. The cone portion 34 is correspondingly recessed in these places.

Two diametrically opposing locking pins 26 are provided below the annular recess 22, protruding radially from the inside of the outer sleeve 16. Two diametrically opposing snap hooks 44 are arranged at the outside of the filter insert 30, including a circumferentially extending snapper arm 46 which is configured to be resilient and arranged such that during rotation of the filter insert 30 within the outer sleeve 12 it moves slidingly over the respective locking pin 26 and then resiliently overlaps it until the locking pin 26 engages in a locking recess 27 in the snapper arm 46. Therein the annular portion 38 of the filter insert 30 is brought into abutment on the step in the annular recess 24 and is thus fixed in correct positional arrangement in the outer sleeve 12. During the rotational movement the snapper arm 46 moves within the annular recess 22.

For detaching the filter insert 30 from the outer sleeve 12 the filter insert 30 is rotated in the opposite direction such that the snap hook 44 disengages from the locking pin 26 and the filter insert 30 can subsequently be extracted from the outer sleeve 12.

Figure 3:
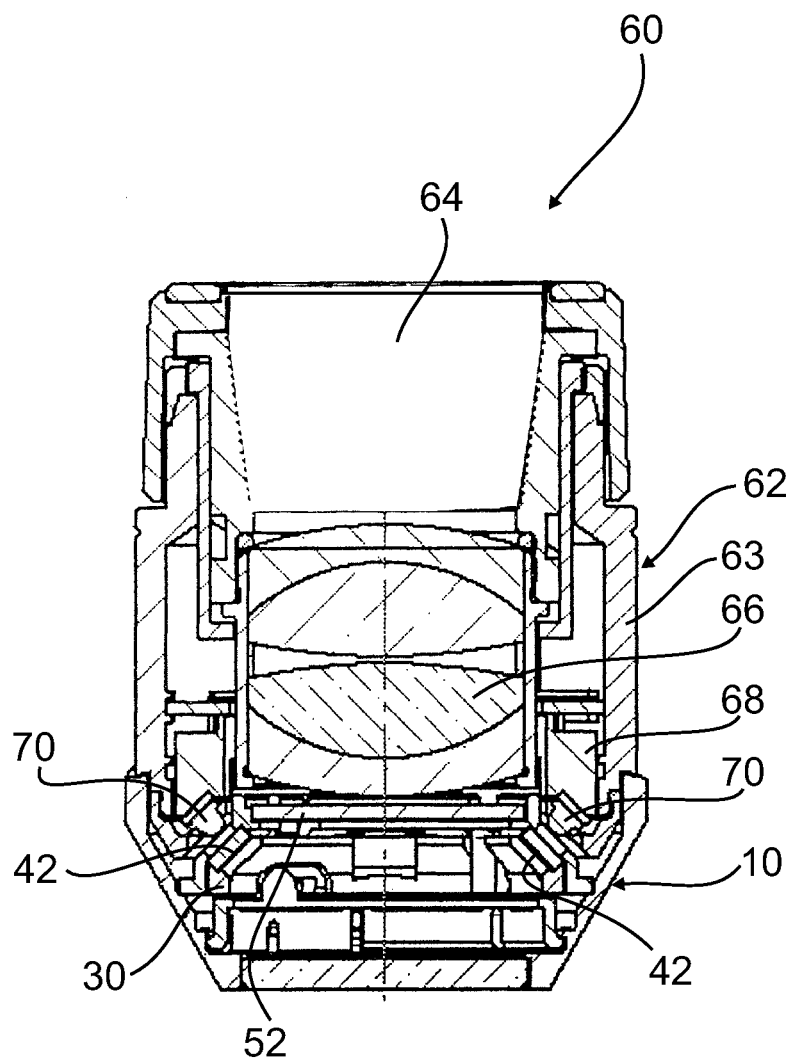
FIG. 3 is a cross-sectional view of a dermatoscope in the region of an illumination head with the spacer attachment of FIG. 1 mounted thereto.

FIG. 3 is a cross-sectional view of a dermatoscope 60 in the region of an illumination head 62. The illumination head 62 includes a generally cylindrical housing 63 and an ocular 64 inserted in the upper end side of the housing 63. The spacer attachment 10 is screwed onto the lower end of the housing 63. An imaging optical system 66 is arranged between the lower end of the ocular 64 and the viewing plate 52 of the spacer attachment 10 and is surrounded at its lower end by a support ring 68, wherein a plurality of LEDs 70 is attached at equal circumferential intervals in the lower end side of the support ring 68 such that each of them is arranged above an illumination window 42, i.e. in front of the respective illumination window 42, as seen in the illumination direction of the LEDs 70.

In a preferred embodiment illumination polarizer filters are arranged in the illumination windows 42, while the viewing plate 52 is formed by a viewing polarizer filter. The two polarizer filters are cross-polarized in order to eliminate reflections.

It is also possible to place neutral density filters in the illumination windows 42 and to provide a viewing plate 52 made of high-quality protective glass. With this solution a brightness can be achieved which is identical to using a polarizer filter. This is important for a diagnosis where a comparison with/without polarization is required.

The viewing plate as well as the illumination windows may also be formed by a circular polarizer filter. In this case positional alignment of the filters is not necessary.

The illumination windows 42 and the viewing plate 52 may also be provided with band-pass filters. Hereby the contrast of certain colors can be increased in order to be able to achieve a safe and fast diagnosis for certain diseases. For example, a green filter which darkens red colors could be used as a band-pass filter. Likewise it is conceivable to use a red filter which darkens green colors.

In the illumination windows 42 use can also be made of fluorescence filters which allow to direct a small strip of UV light onto the viewing plane and excite luminophores to generate light. As the viewing plate a filter adapted for the respective luminophore may be used which improves the signal-to-noise ratio and thus the contrast. In this case corresponding contrast agents could be employed to perform an angiographic examination (vascular imaging, subcutaneous blood vessel imaging).

The invention claimed is:

1. A spacer attachment for a dermatoscope, comprising an outer sleeve having an attachment end configured for releasable attachment to an illumination head of a dermatoscope, and a contact end intended to be placed on a skin of a patient at an examination location, wherein
a filter insert is releasably attached in said outer sleeve by rotation about a central axis of said outer sleeve and by means of a rotation snap device comprising at least one resilient snap hook which is arranged at the outer circumference of said filter insert and resiliently engages around a projection provided at an inner wall of said outer sleeve,
said filter insert including a viewing plate intersected perpendicularly by said central axis of said outer sleeve.

2. The spacer attachment according to claim 1, wherein said filter insert includes a window ring surrounding said viewing plate and having several light-transmissive illumination windows arranged therein.

3. A spacer attachment according to claim 2, wherein an illumination polarizer filter is arranged in said illumination windows.

4. A spacer attachment according to claim 1, wherein said viewing plate is a viewing polarizer filter.

5. A spacer attachment according to claim 2, wherein an illumination polarizer filter is arranged in said illumination windows and said viewing plate is a viewing polarizer filter, said illumination polarizer filters being cross-polarized relative to said viewing polarizer filter.

6. A spacer attachment according to claim 1, wherein the contact end of said outer sleeve is closed by a transparent contact plate.

7. A kit comprising
a spacer attachment for a dermatoscope, said spacer attachment including an outer sleeve having an attachment end configured for releasable attachment to an illumination head of a dermatoscope, and a contact end intended to be placed on a skin of a patient at an examination location, and
several mutually exchangeable filter inserts which are adapted to be releasably attached in said outer sleeve by rotation about a central axis of said outer sleeve and by means of a rotation snap device comprising at least one resilient snap hook which is arranged at the outer circumference of said filter insert and resiliently engages around a projection provided at an inner wall of said outer sleeve,
said filter inserts including a viewing plate intersected perpendicularly by said central axis of said outer sleeve when attached to said outer sleeve.

8. The kit according to claim 7, wherein said filter inserts are provided with at least one of a neutral density filter, a circular polarizer filter, a band-pass filter and a fluorescence filter.

9. The kit according to claim 7, wherein at least one of said filter inserts includes a window ring surrounding said viewing plate and having several light-transmissive illumination windows arranged therein.

10. The kit according to claim 9, wherein an illumination polarizer filter is arranged in said illumination windows and said viewing plate is a viewing polarizer filter, said illumination polarizer filters being cross-polarized relative to said viewing polarizer filter.

11. A dermatoscope comprising an illumination head having an illumination side to which a spacer attachment is attached, said spacer attachment comprising an outer sleeve having an attachment end configured for releasable attachment to the illumination head of a dermatoscope, and a contact end intended to be placed on a skin of a patient at an examination location, wherein
a filter insert is releasably attached in said outer sleeve by rotation about a central axis of said outer sleeve and by means of a rotation snap device comprising at least one resilient snap hook which is arranged at the outer circumference of said filter insert and resiliently engages around a projection provided at an inner wall of said outer sleeve,
said filter insert including a viewing plate intersected perpendicularly by a central axis of said outer sleeve.

12. The dermatoscope according to claim 11, wherein said filter insert includes a window ring surrounding said viewing plate and having several light-transmissive illumination windows arranged therein, illuminants being arranged at the illumination side of said illumination head in front of each illumination window of said filter insert, as seen in a illumination direction of said illuminants.

13. The dermatoscope according to claim 12, wherein said illuminants are LEDs.

14. The dermatoscope according to claim 12, wherein an illumination polarizer filter is arranged in said illumination windows and said viewing plate is a viewing polarizer filter, said illumination polarizer filters being cross-polarized relative to said viewing polarizer filter.

* * * * *